(12) United States Patent
Dirckx et al.

(10) Patent No.: US 12,193,865 B2
(45) Date of Patent: Jan. 14, 2025

(54) X-RAY SENSOR

(71) Applicant: Adaptix Ltd., Begbroke (GB)

(72) Inventors: Conrad Dirckx, Begbroke (GB); Sami Mughal, Begbroke (GB)

(73) Assignee: ADAPTIX LTD, Begbroke (GB)

( * ) Notice: Subject to any disclaimer, the term of this patent is extended or adjusted under 35 U.S.C. 154(b) by 157 days.

(21) Appl. No.: 17/902,343

(22) Filed: Sep. 2, 2022

(65) Prior Publication Data

US 2022/0409157 A1 Dec. 29, 2022

Related U.S. Application Data

(63) Continuation of application No. PCT/IB2021/051735, filed on Mar. 2, 2021.

(30) Foreign Application Priority Data

Mar. 2, 2020 (GB) ...................................... 2002989

(51) Int. Cl.
| | |
|---|---|
| A61B 6/00 | (2024.01) |
| A61B 6/02 | (2006.01) |
| A61B 6/42 | (2024.01) |
| A61B 6/51 | (2024.01) |

(52) U.S. Cl.
CPC .............. *A61B 6/527* (2013.01); *A61B 6/025* (2013.01); *A61B 6/4233* (2013.01); *A61B 6/51* (2024.01); *A61B 6/512* (2024.01); *A61B 6/5264* (2013.01); *A61B 6/547* (2013.01); *A61B 6/56* (2013.01)

(58) Field of Classification Search
CPC ....... A61B 6/527; A61B 6/025; A61B 6/4233; A61B 6/51; A61B 6/512; A61B 6/5264; A61B 6/547; A61B 6/56
See application file for complete search history.

(56) References Cited

U.S. PATENT DOCUMENTS

| | | | |
|---|---|---|---|
| 9,314,216 B2 | 4/2016 | De Godzinsky | |
| 9,986,964 B2 | 6/2018 | Kravis et al. | |
| 10,376,227 B2 | 8/2019 | Brenner | |
| 10,610,175 B2 | 4/2020 | Maurer, Jr. | |
| 11,903,753 B2 | 2/2024 | Schulze-Ganzlin et al. | |
| 2006/0257816 A1 | 11/2006 | Klemola et al. | |

(Continued)

FOREIGN PATENT DOCUMENTS

| | | |
|---|---|---|
| EP | 1000582 | 6/2000 |
| EP | 3235430 | 10/2017 |

(Continued)

OTHER PUBLICATIONS

UKIPO, Examination Report in corresponding GB application GB2002989.8, Nov. 10, 2023.

(Continued)

*Primary Examiner* — David P Porta
*Assistant Examiner* — Casey Bryant
(74) *Attorney, Agent, or Firm* — Alley IP

(57) ABSTRACT

To produce 3D x-ray images, it is necessary to compensate for patient movement during the emission and detection of x-rays; this may be achieved by providing an x-ray sensor 20 comprising a digital x-ray detector 40, and an inertial sensor 50, 60 for providing positional information relating to changes in the relative position of the x-ray sensor during detection of x-rays.

20 Claims, 5 Drawing Sheets

(56) References Cited

U.S. PATENT DOCUMENTS

| | | | | |
|---|---|---|---|---|
| 2012/0008735 | A1* | 1/2012 | Maurer | A61B 6/488 |
| | | | | 378/5 |
| 2014/0120493 | A1 | 5/2014 | Levin | |
| 2015/0038840 | A1* | 2/2015 | Hassan | A61B 6/4283 |
| | | | | 600/436 |
| 2015/0305696 | A1* | 10/2015 | Yamakawa | G06T 11/006 |
| | | | | 378/19 |
| 2018/0070898 | A1 | 3/2018 | Kravis et al. | |
| 2022/0133245 | A1* | 5/2022 | Wells | A61B 5/08 |
| | | | | 382/132 |
| 2022/0151576 | A1 | 5/2022 | Subramanyan et al. | |

FOREIGN PATENT DOCUMENTS

| | | | |
|---|---|---|---|
| EP | 3673810 | 7/2020 | |
| JP | 2008-253569 | 10/2008 | |
| JP | 2010-179094 | 8/2010 | |
| JP | 2014-508619 | 4/2014 | |
| JP | 2015-514983 | 5/2015 | |
| JP | 2014-505548 | 6/2016 | |
| JP | 2016-168327 | 9/2016 | |
| JP | 2019-514663 | 6/2019 | |
| JP | 2019-180941 | 10/2019 | |
| JP | 2019-528099 | 10/2019 | |
| JP | 2022-514814 | 2/2022 | |
| JP | 2022-526086 | 5/2022 | |
| WO | WO-2011156526 A2 * | 12/2011 | A61B 5/055 |
| WO | 2012/008492 | 1/2012 | |
| WO | 2017/196413 | 11/2017 | |
| WO | 2019/038304 | 2/2019 | |
| WO | WO-2019038304 A1 * | 2/2019 | A61B 5/0066 |
| WO | 2020/185823 | 9/2020 | |

OTHER PUBLICATIONS

UKIPO, Search Report in corresponding GB application GB2002989.8, Aug. 21, 2020.

WIPO, International Search Report and Written Opinion in corresponding PCT application PCT/IB2021/051735, May 28, 2021.

JPO, Office Action in corresponding JP application 2022-552589, Oct. 6, 2024.

* cited by examiner

X-RAY SENSOR

RELATED APPLICATIONS

This application claims the benefit under 35 U.S.C. § 120, and is a continuation, of co-pending International Application PCT/IB2021/051735, filed Mar. 2, 2021 and designating the US, which claims priority to GB Application 2002989.8, filed Mar. 2, 2020, such GB Application also being claimed priority to under 35 U.S.C. § 119. These GB and International applications are incorporated by reference herein in their entireties.

FIELD

The present invention relates generally to an x-ray sensor and a method of producing x-ray images and finds particular, although not exclusive, utility in intraoral x-ray imaging technology.

BACKGROUND

Digital intraoral x-ray sensors in combination with conventional x-ray sources are known for producing dental x-rays. This type of equipment produces low-doses of x-rays. The sensors typically have pixel sizes as small as 20×20 µm. The acquisition times are typically of the order of 0.1-0.2 seconds such that patient motion does not generally impact on image quality. However, the resulting images are 2-dimensional.

It is desirable to have 3-dimension images in certain circumstances. These can be produced using a combination of an array of x-ray sources in combination with an intraoral digital x-ray sensor; with the resulting data being processed to produce 3-dimension intraoral images using digital tomosynthesis. However, to achieve this, the acquisition times are typically in the range of 1-10 seconds. Consequently, patient motion impacts on the quality of the resulting images.

This is also the case in extraoral dental x-ray procedures such as panoramic or CBCT systems where an acquisition can take between 5-40 seconds depending on the system and the protocol used.

Further still, it is recognized that some patient motion will always occur, including head motion of perhaps 80 µm due to changes in blood pressure during a cardiac cycle.

One method to overcome this problem of patient movement is to mechanically attach the intraoral sensor to the x-ray source. However, this affects the operator's ability to position the sensor in the correct location, leading in turn to a reduction in patient comfort.

Accordingly, it is desirable to have a system of producing dental images using an intraoral sensor and an external x-ray source, without any mechanical connection between the two, such that 3-dimensional x-ray images can be produced with relatively good clarity and lack of blurring even though the patient's head moves during the acquisition stage.

SUMMARY

In a first aspect, the invention provides an x-ray sensor comprising a digital x-ray detector, and an inertial sensor for providing positional information relating to changes in the relative position of the x-ray sensor during detection of x-rays.

The x-ray sensor may be configured to be moved physically independently of one or more x-ray emitters. Alternatively, or additionally, the x-ray sensor may be configured to be moved physically independently of one or more x-ray emitter arrays.

The inertial sensor may comprise at least one accelerometer and/or at least one gyroscope. The inertial sensor may be integral with the x-ray detector or may be releasably attachable thereto. Such inertial sensors are relatively small and low-cost. For instance, these sensors can be as small as 2×2×1 mm such that they can be readily integrated into an intraoral sensor which has external dimensions of approximately 32×44×10 mm.

The inertial sensors are capable of providing a stream of accurate 3-axis acceleration & orientation data which in turn can be used to track changes in the spatial position of the inertial sensor, and thus the x-ray detectors, as each image is acquired.

The x-ray sensor may include a processor, or "emitter displacement calculation unit" for using the stream of data from the inertial sensor, together with timing signals to calculate positional offset information (relative to a starting position), correcting for errors in the inertial sensor data, for each image acquisition. The processor may also be an "image reconstruction unit" for using the detected x-rays, the nominal positions of the x-ray sources and the positional offset information to thereby calculate the resultant x-ray images.

The processor may be arranged to calculate a motion correction factor, to be applied to one or more x-ray images, based on the positional information. This calculation may be performed by the processor which may be synchronized with an acquisition control system and which may perform integration of the inertial sensor data together with an error correction.

The processor may include the acquisition control system.

The processor may be arranged to create the 2-dimensional, and/or 3-dimensional, images by taking account of changes in the relative position of the intraoral x-ray sensor during detection of x-rays.

The displacement of the sensor during the acquisition stage may be calculated from the positional data using known methods.

The processor may be integral with the sensor. Alternatively, the processor may be external to the sensor. Another option is that the processing is undertaken by more than one processor, being located in the sensor and external to the sensor. For instance, the emitter displacement calculation unit may be arranged onboard with the x-ray sensor, and the image reconstruction unit may be arranged external to the x-ray sensor and possibly with the acquisition control system.

The x-ray sensor may further comprise communication means, such as a transmitter, for transmitting data acquired by the detector and the positional information to the processor. Such communication means include wired and wireless equipment such as radio frequency transmitters and receivers.

The x-ray sensor may include means for of maintaining it stationary relative to the region of interest. This may include straps, cords, and other such means which enable it to be temporarily attached, and fixed positionally relative, to a subject who/which may move during the procedure.

The x-ray sensor may be an intraoral sensor arranged to fit within a human mouth. In this way, intraoral x-ray images may be created. The x-ray sensor may be sized appropriately to fit in a human mouth. For instance, it may have a maximum dimension in any one orthogonal axis of 3 cm. The x-ray sensor may further comprise a bite bar for maintaining the detector in relatively fixed relationship to the mouth of a subject during use. Other means of maintaining it stationary relative to teeth are contemplated such as clamps, grips, and substrates including parts molded to an approximate shape of the teeth. These means, such as the bite bar, may be integral with the x-ray sensor or be releasably attachable. For instance, they may form part of a frame provided around all or part of the x-ray sensor. It is also contemplated that the frame may, in one example, include the inertial sensor.

Once the intraoral x-ray sensor is positioned inside the mouth, it will not then typically move relative to the teeth during whole head motion. Therefore, any intraoral x-ray sensor motion relative to an external x-ray source will also directly apply to the teeth. For this reason, during the image creation process, the calculated translation and rotation of the sensor (R) can be applied as the inverse (R') to the nominal x-ray source position and orientation for that image. This means that the image creation process does not create an image of the teeth as they would have appeared from the sensor position if there had been no motion. Rather, the process creates an image of the teeth as they appear from the actual relative position and relative orientation. In the case of a tomosynthesis acquisition of multiple images, this positional information is then be integrated into the reconstruction algorithm to accurately determine the relative position of the emitter and detector for each image.

Furthermore, the positional information may be used to determine the degree of motion experienced during the acquisition of each individual image. The processor may also be arranged to provide an indication to an operator when motion of the intraoral sensor, during use, exceeds a predetermined value. Furthermore, the processor may be arranged to automatically exclude data acquired by the detector when motion of the intraoral sensor, during use, exceeds a predetermined value. The intraoral x-ray sensor may further be arranged to automatically emit and detect additional x-rays to "re-scan" an area for which previous image are likely to be blurry due to this excessive motion of the patient's head.

The above discussion concerning the calculated translation and rotation of the x-ray sensor, the determination of the degree of motion experienced during the acquisition of each individual image, and the provision of an indication to an operator, may also apply to x-ray sensors, not being intraoral x-ray sensors, which are placed externally of the subject during use.

The x-ray sensor may be arranged in combination with one or more x-ray emitters. The emitters may be arranged in a panel including an array of individually energizable x-ray emitters, which may be described as a distributed array of x-ray sources. The use of a distributed array of x-ray sources may allow each emitter to be individually electronically triggered which may be much faster than having to physically move a single x-ray source.

Unlike CBCT, where x-rays may be emitted over a complete 360-degree sweep around the patient, digital tomosynthesis may only cover a partial sweep. The x-ray sensor and its method of use may allow for stationary tomosynthesis (sDT); the partial sweep being achieved possibly without physical movement of the x-ray source; instead, possibly being achieved by triggering a series of the spatially distributed fixed sources, in the array, fired in a sequence.

The array of x-ray emitters may be a single flat panel source (FPS). The x-ray detector may be a flat panel x-ray detector (FPD). It is expected that in use, for the imaging of a single tooth, the FPS may remain stationary relative to the environment, and remain stationary relative to the subject, assuming the subject does not move. This may also be the case for groups of immediately adjacent teeth, assuming the detector is large enough. Since the FPS includes an array of emitters, x-rays may be emitted from various positions to create enough data to produce a 3D image. However, if a single source x-ray emitter is used then the x-ray source may have to move during the procedure if 3D images are required; however, this may not be the case if only 2D images are required.

In a second aspect, the invention provides a method of producing x-ray images, the method comprising the steps of fixing the position of the x-ray sensor relative to the region of interest; emitting x-rays from an x-ray source towards the x-ray sensor; operating the x-ray sensor to detect said x-rays; and processing said detected x-rays to produce images of the region of interest.

The x-ray sensor may include a bite bar, the region of interest may include at least one tooth, and the step of fixing the position of the x-ray sensor relative to the region of interest may include placing the x-ray sensor in the mouth of a subject and the subject holding the bite bar between their teeth.

The positional information provided by the inertial sensor may be used to determine the relative position of the x-ray source and the digital x-ray detector for each image.

The processor may calculate a motion correction factor based on the relative position of the x-ray source and the digital x-ray detector for each image.

The detection of said x-rays may occur without any mechanical connection between the x-ray sensor and x-ray source.

The x-ray sensor and its method of use permit accurate post-acquisition motion compensation which does not suffer from the limitations of image-based motion compensation where displacement parallel to a central axis of the x-ray beam or rotation around that beam are relatively difficult to calculate when trying to register different 2D projection images from different positions of a 3D object. They do not require any mechanical attachment between the x-ray source and x-ray detector which in turn makes for relatively faster image acquisition and relatively greater convenience for the operator and the patient.

Accurate motion compensation reduces or eliminates image artefacts due to motion. This may lead to a reduction in, or elimination of, misinterpretation or misdiagnosis.

Further processing of resulting images may also be undertaken based on presently known image analysis and image-based motion compensation to provide even finer levels of motion compensation.

BRIEF DESCRIPTION OF THE DRAWINGS

The above and other characteristics, features and advantages of the present invention will become apparent from the following detailed description, taken in conjunction with the accompanying drawings, which illustrate, by way of example, the principles of the invention in relation to intraoral x-ray imaging. This description is given for the sake of example only, without limiting the scope of the invention. The reference figures quoted below refer to the attached drawings.

DETAILED DESCRIPTION

Figure 1:
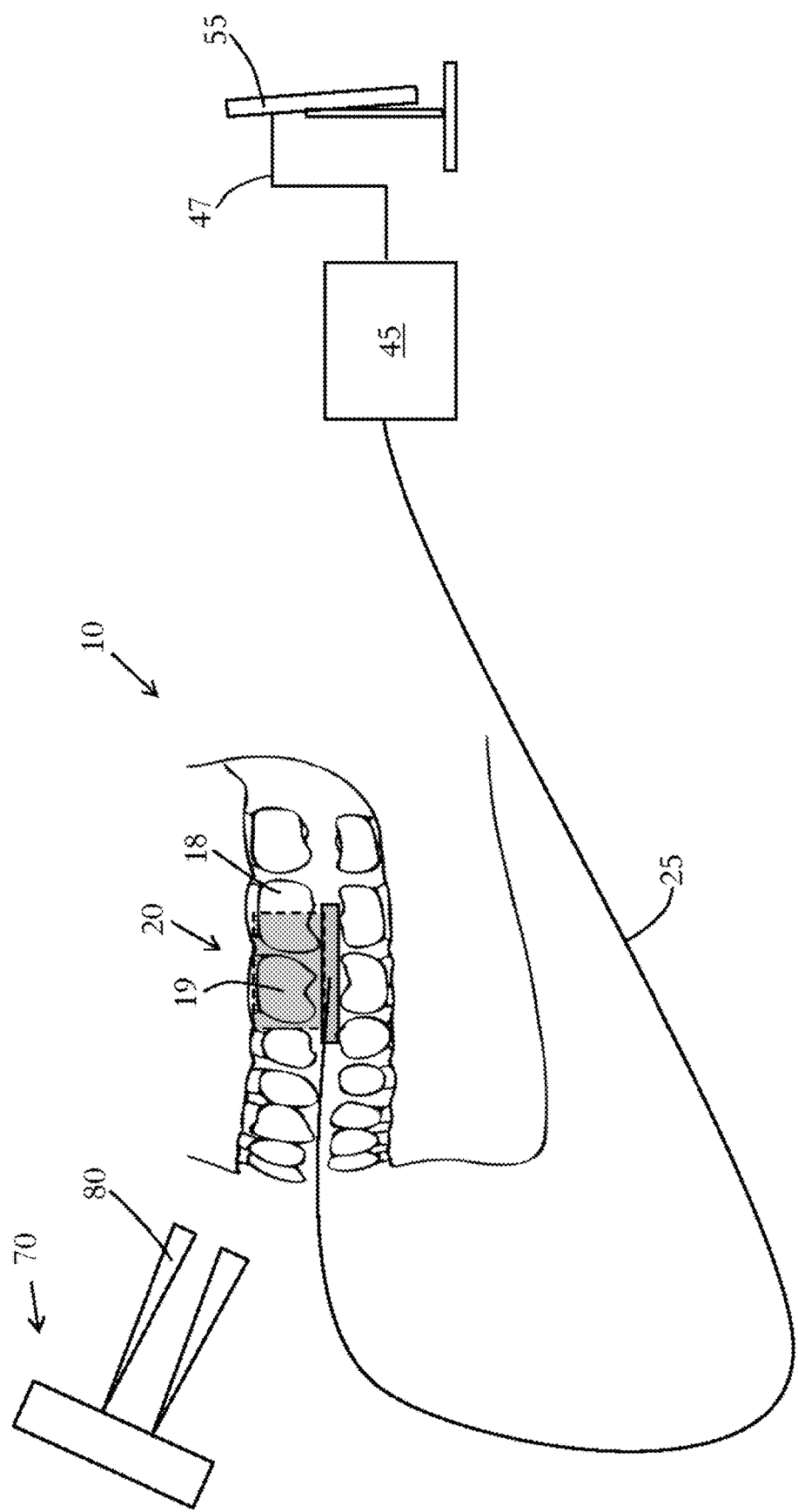
FIG. 1 is a schematic view of an intraoral x-ray sensor inside a patient's mouth being exposed to x-rays.

The present invention will be described with respect to certain drawings but the invention is not limited thereto but only by the claims. The drawings described are only schematic and are non-limiting. Each drawing may not include all of the features of the invention and therefore should not necessarily be considered to be an embodiment of the invention. In the drawings, the size of some of the elements may be exaggerated and not drawn to scale for illustrative purposes. The dimensions and the relative dimensions do not correspond to actual reductions to practice of the invention.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that operation is capable in other sequences than described or illustrated herein. Likewise, method steps described or claimed in a particular sequence may be understood to operate in a different sequence.

Moreover, the terms top, bottom, over, under and the like in the description and the claims are used for descriptive purposes and not necessarily for describing relative positions. It is to be understood that the terms so used are interchangeable under appropriate circumstances and that operation is capable in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Similarly, it is to be noticed that the term "connected", used in the description, should not be interpreted as being restricted to direct connections only. Thus, the scope of the expression "a device A connected to a device B" should not be limited to devices or systems wherein an output of device A is directly connected to an input of device B. It means that there exists a path between an output of A and an input of B which may be a path including other devices or means. "Connected" may mean that two or more elements are either in direct physical or electrical contact, or that two or more elements are not in direct contact with each other but yet still co-operate or interact with each other. For instance, wireless connectivity is contemplated.

Reference throughout this specification to "an embodiment" or "an aspect" means that a particular feature, structure or characteristic described in connection with the embodiment or aspect is included in at least one embodiment or aspect of the present invention. Thus, appearances of the phrases "in one embodiment", "in an embodiment", or "in an aspect" in various places throughout this specification are not necessarily all referring to the same embodiment or aspect, but may refer to different embodiments or aspects. Furthermore, the particular features, structures or characteristics of any one embodiment or aspect of the invention may be combined in any suitable manner with any other particular feature, structure or characteristic of another embodiment or aspect of the invention, as would be apparent to one of ordinary skill in the art from this disclosure, in one or more embodiments or aspects.

Similarly, it should be appreciated that in the description various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Moreover, the description of any individual drawing or aspect should not necessarily be considered to be an embodiment of the invention. Rather, as the following claims reflect, inventive aspects lie in fewer than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some features included in other embodiments, combinations of features of different embodiments are meant to be within the scope of the invention, and form yet further embodiments, as will be understood by those skilled in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

In the discussion of the invention, unless stated to the contrary, the disclosure of alternative values for the upper or lower limit of the permitted range of a parameter, coupled with an indication that one of said values is more highly preferred than the other, is to be construed as an implied statement that each intermediate value of said parameter, lying between the more preferred and the less preferred of said alternatives, is itself preferred to said less preferred value and also to each value lying between said less preferred value and said intermediate value.

The use of the term "at least one" may mean only one in certain circumstances. The use of the term "any" may mean "all" and/or "each" in certain circumstances.

The principles of the invention will now be described by a detailed description of at least one drawing relating to exemplary features. It is clear that other arrangements can be configured according to the knowledge of persons skilled in the art without departing from the underlying concept or technical teaching, the invention being limited only by the terms of the appended claims.

FIG. 1 shows a schematic side view of a set of teeth 10 being exposed to x-rays 80 being emitted by an x-ray source 70. The patient has an intraoral x-ray sensor 20 in their mouth. The sensor 20 is connected by a cable 25 to a processor 45 which in turn is connected to a display 55 by cable 47.

The sensor 20 is adjacent two teeth 18, 19. In use, the x-ray source may emit a stream of x-rays from various emitters arranged within it. The x-rays may pass through the teeth 18, 19 and be detected by the sensor 20. The detector may pass the resultant digital data to the processor 45 for processing to create 2D and/or 3D images on the display 55.

Figure 2:
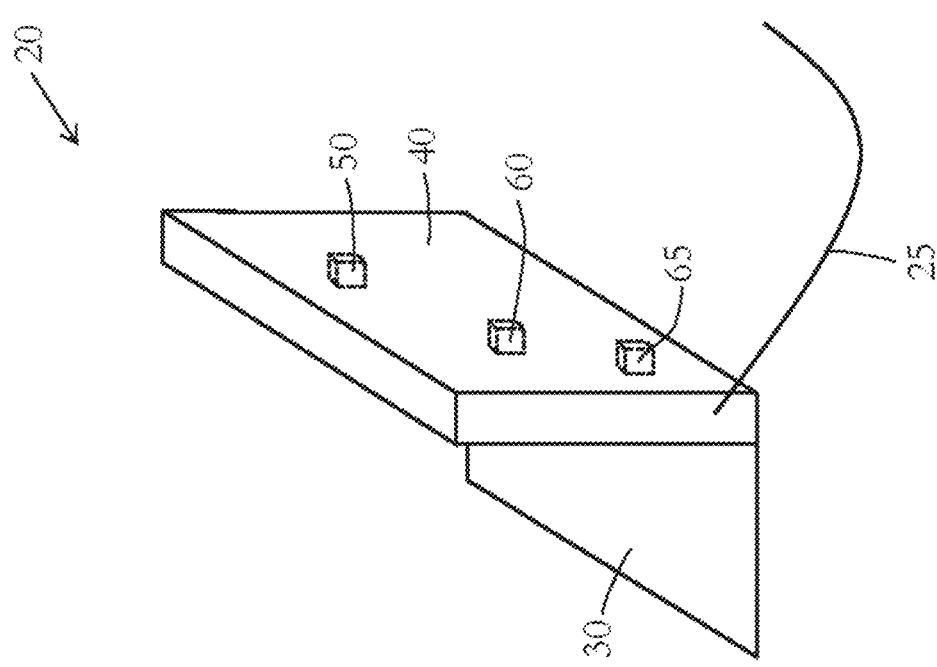
FIG. 2 is a perspective view of an intraoral x-ray sensor.

An example of how an intraoral sensor 20 may appear is shown in FIG. 2. The sensor 20 comprises the detector part 40, which is cuboid in appearance, and a relatively flat and planar "bite bar" 30 which extends perpendicularly outward from one end of the detector part 40 such that, in use, the bar may be held firmly between the patient's upper and lower teeth to thereby maintain the sensor in fixed relationship to the teeth.

The detector part 40 includes an accelerometer 50 and gyroscope 60. It is contemplated that a processor 65 may also be included for processing some or all of the data produced by any, or all of the accelerometer 50, gyroscope 60, and x-ray detector 40.

A cable 25 is shown for communication to an external processor 45 and/or display 55, if required.

Figure 3:
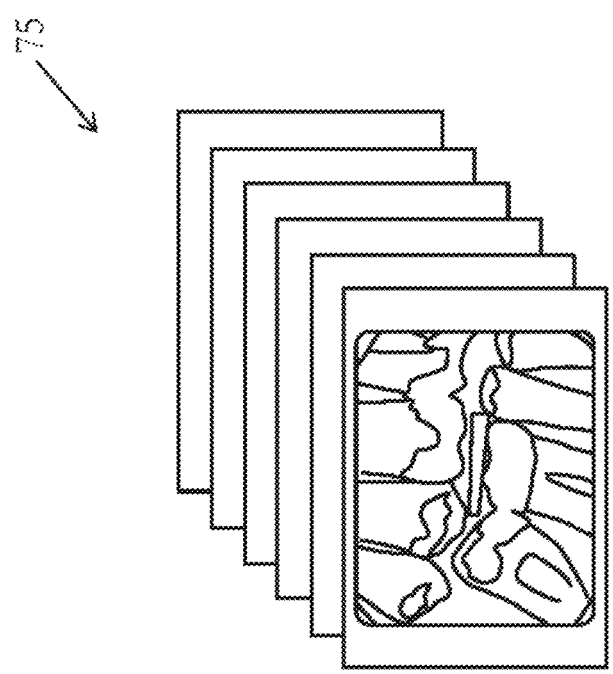
FIG. 3 is a representation of a series of x-ray images for use in creating a 3D digital tomosynthesis image.

The processor(s) 45, 65 are arranged to produce 2D and/or 3D x-ray images of the teeth which is indicated by a series of images 75 in FIG. 3.

Figure 4:
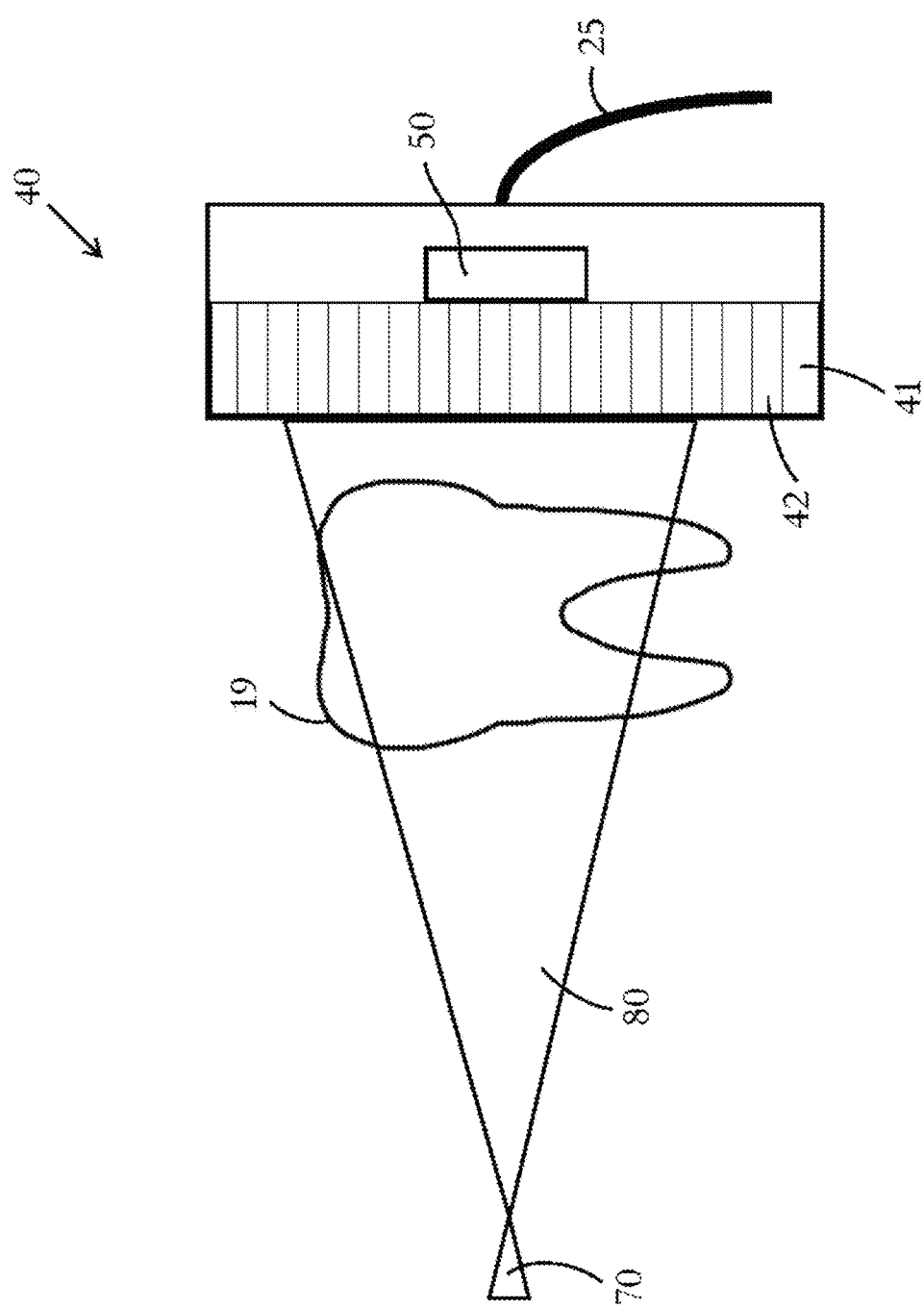
FIG. 4 is a schematic view of a tooth being x-rayed.

A schematic view of a detector 40 is shown in FIG. 4. The detector 40 comprises a plurality of detector pixels 41, 42 etc. arranged therein for detecting x-rays.

The accelerometer 50 is also indicated within the detector 40.

A tooth 19 is shown being subjected to a cone shape of x-rays 80 emitted by the x-ray emitter 70. The cone shape of x-rays 80 meets the plurality of pixels 41, 42 in the detector 40 such that an x-ray image of the tooth may be produced once the data has been processed. The image may well appear similar to the one shown in FIG. 6.

Figure 5:
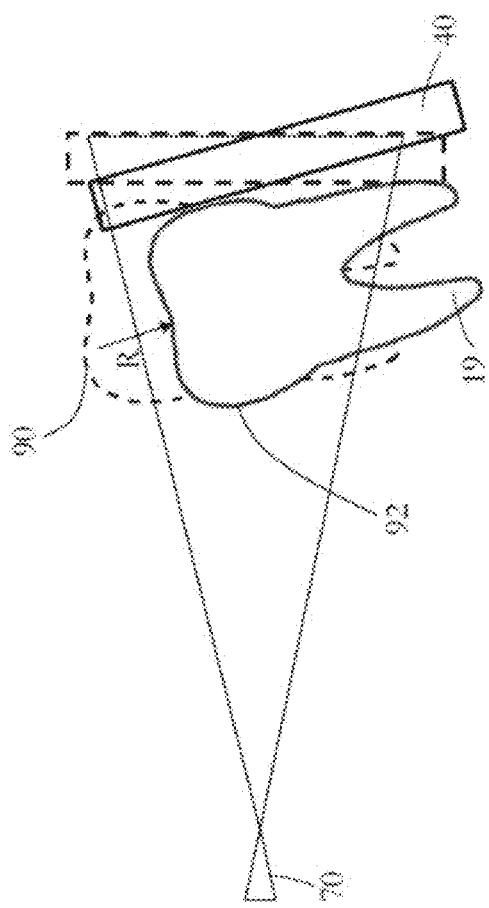
FIGS. 5 and 6 are schematic views of a tooth being x-rayed before and after movement of the patient.

In FIG. 5, the same tooth 19 has been rotated slightly due to patient movement. The new position 92 is contrasted with the previous position 90 shown in broken lines. Due to the bite bar holding the sensor 40 fixed relative to the teeth it can be seen how the sensor has also moved; its previous position also being shown in broken lines. If the image received by the detector 40, as a result of the x-rays emitted by x-ray emitter 70, were to be combined with images taken with the tooth not having been moved, such as shown in FIG. 4, the resulting 3D image would be incorrect. This is because although the tooth and detector have moved, the x-ray emitter has remained stationary. Accordingly, the image needs to be processed to provide an image which can be combined with the FIG. 4 image.

Figure 6:
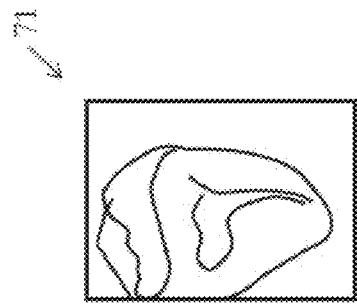
Figure 6:
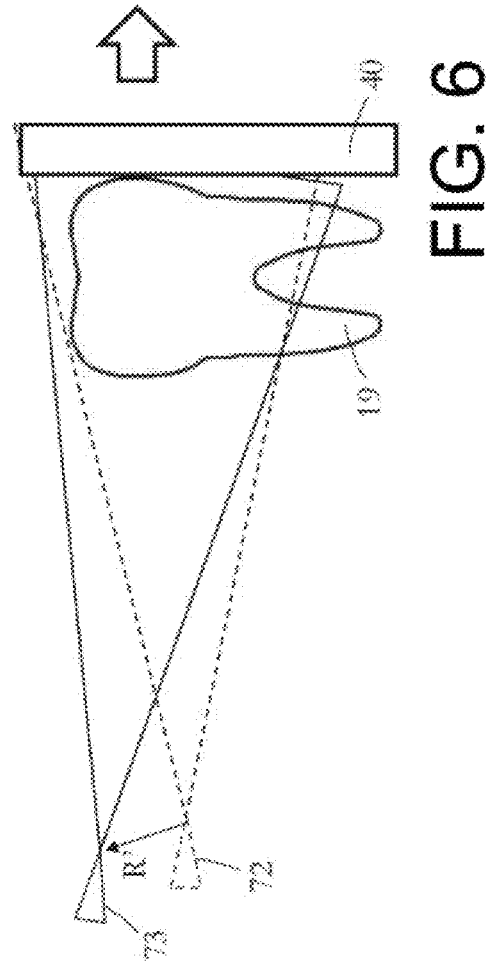

FIG. 6 shows how this processing may take account of the movement of the tooth 19 and sensor 20 to create an identical, or virtually identical, image 72. The movement of the tooth in FIG. 5 away from the previous (FIG. 4) position is represented by "R". In FIG. 6, the data is processed such that the image is created as though the x-ray emitter 70 had been moved by R' and was in the position 73, rather than its actual position 72, as shown in outline. The resultant image 71 is produced which can then be combined with the other images. Each image can be processed and adjusted such that patient movement can be compensated so that all the images are combinable as if no patient movement had occurred. The movement of the emitter R' and movement of the tooth R are proportional to one another, therefore, measurement of R may be used to calculate R'.

The movement R of the tooth is determined by data sent from the accelerometer 50 and gyroscope 60, located within the sensor 20.

Figure 7:
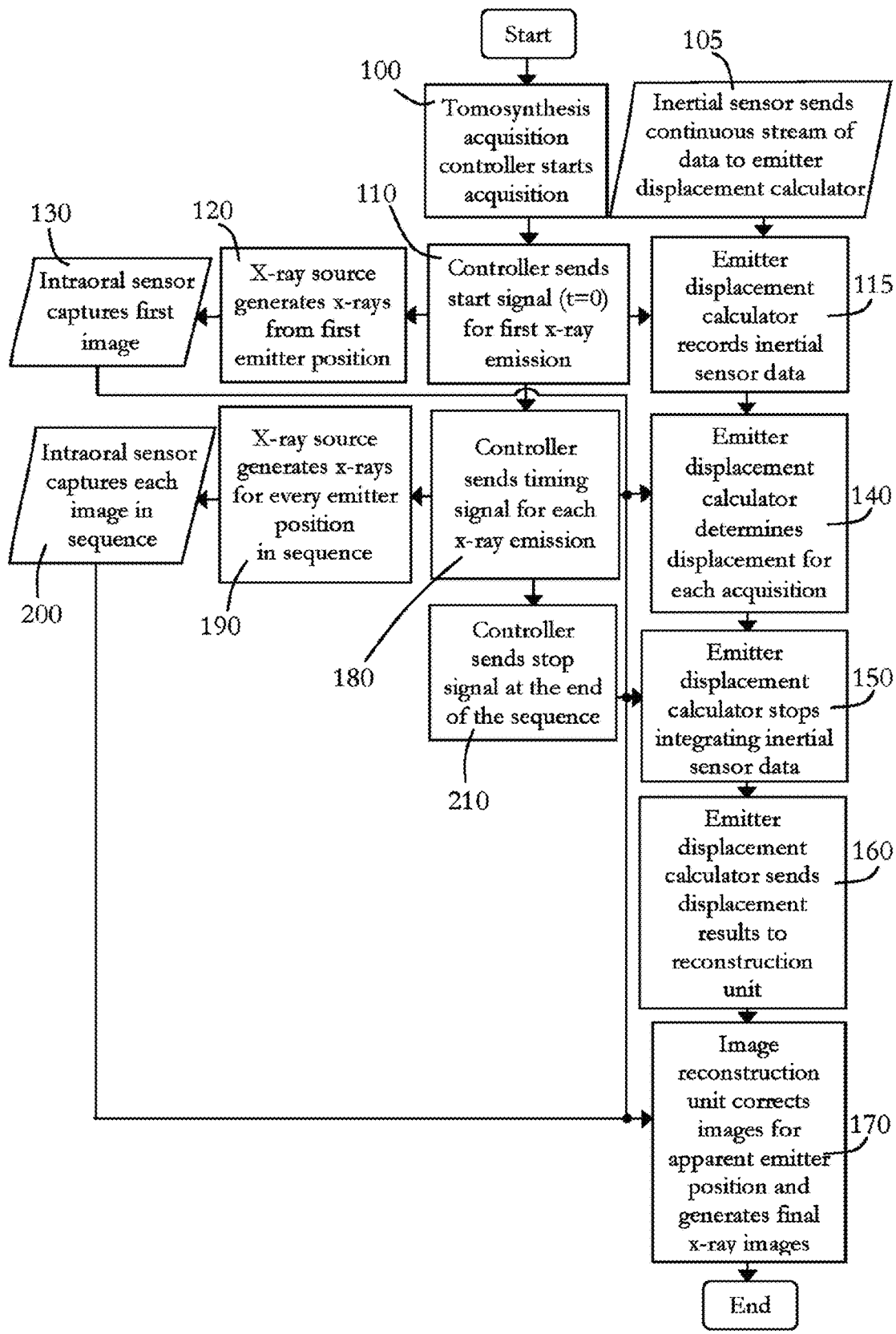
FIG. 7 is a flow chart depicting a method of operation of an x-ray sensor and subsequent image generation.

In FIG. 7, a method of operation is depicted. In step 100 the tomosynthesis acquisition controller starts operation. The controller sends 110 a start signal (t=0) for the first x-ray emission. In step 120, the x-ray source generates x-rays from the emitter position. In step 130, the intraoral sensor captures the first x-ray image. Simultaneously with the emitters emitting x-rays the inertial sensor sends 105 a continuous stream of data to the emitter displacement calculator. The emitter displacement calculator records 115 the inertial sensor data. The emitter displacement calculator determines 140 displacement for each acquisition relative to the starting position. The emitter displacement calculator stops 150 integrating the inertial sensor data. The emitter displacement calculator sends 160 data to the image reconstruction unit. The image reconstruction unit corrects the images for apparent emitter position and generates 170 final x-ray images.

The controller sends 180 timing signals for each subsequent x-ray emission event (for the creation of a new image). The x-ray sources generate 190 x-rays for every emitter position in the sequence. The intraoral sensor captures 200 each image in the sequence of images and sends the data to the image reconstruction unit where final x-ray images are generated 170 after having been corrected for apparent emitter position. That is, corrected for the position that x-rays are apparently emitted from. For example, a plurality of emitters, or more specifically an FPS, include emitters in multiple physical locations and x-rays may be emitted from apparent positions, or various combinations of, these emitters to create data to produce a 3D image. These various or apparent positions may be formed by energizing more than one emitter synergistically. By way of example, energizing more than one emitter at the same time or with overlapping time periods is energizing more than one emitter synergistically.

It is to be understood that it may not be necessary to know the absolute position of the x-ray emitter relative to any fixed datum forming part of the patient, or outside the patient, since it is only the changes in position of the patient relative to a starting point that matter. However, if desired, a starting position could be recorded such that movement of the sensor relative to that position may be calculated.

In the foregoing, the use of the singular "tooth" may include the plural "teeth" and vice-versa.

The invention claimed is:

1. An x-ray sensor for tomosynthesis imaging comprising:
a digital x-ray detector;
an inertial sensor for providing positional information relating to changes in the relative position of the x-ray sensor during detection of x-rays; and
an emitter displacement calculation unit configured to calculate positional offset information relative to a starting position, based on timing signals and data from the inertial sensor.

2. The x-ray sensor of claim 1, wherein the inertial sensor comprises at least one accelerometer and/or at least one gyroscope.

3. The x-ray sensor of claim 1, in combination with a processor for processing data acquired by the detector and the positional information to thereby create 2-dimensional, and/or 3-dimensional, images.

4. The sensor of claim 3, wherein the processor is arranged to calculate a motion correction factor based on the positional information.

5. The sensor of claim 4, wherein the processor is arranged to create the 2-dimensional, and/or 3-dimensional, images by taking account of changes in the relative position of the x-ray sensor during detection of x-rays.

6. The x-ray sensor of claim 3, further comprising a transmitter for transmitting data acquired by the detector and the positional information to the processor.

7. The x-ray sensor of claim 6, wherein the processor is arranged to provide an indication to an operator when motion of the sensor, during use, exceeds a predetermined value.

8. The x-ray sensor of claim 6, wherein the processor is arranged to automatically exclude data acquired by the detector when motion of the sensor, during use, exceeds a predetermined value.

9. The x-ray sensor of claim 1, in combination with one or more x-ray emitters.

10. The x-ray sensor of claim 9, wherein the one or more x-ray emitters are arranged as a distributed array of x-ray sources, and wherein each emitter is configured to be individually triggered electronically.

11. The x-ray sensor of claim 1, being an intraoral sensor arranged to fit within a human mouth.

12. The x-ray sensor of claim 11, further comprising a bite bar for maintaining the detector in relatively fixed relationship to the mouth of a subject during use.

13. The x-ray sensor of claim 1, wherein the sensor is configured to be moved physically independently of one or more x-ray emitters.

14. The x-ray sensor of claim 1 comprising an image reconstruction unit configured to calculate resultant x-ray images based on the detected x-rays, nominal positions of x-ray sources and the positional offset information.

15. A method of producing x-ray images, the method comprising the steps of providing an x-ray sensor according to claim 1; fixing the position of the x-ray sensor relative to the region of interest; emitting x-rays from an x-ray source towards the x-ray sensor; operating the x-ray sensor to detect said x-rays; and processing said detected x-rays to produce images of the region of interest.

16. The method of claim 15, wherein the x-ray sensor includes a bite bar, the region of interest includes at least one tooth, and the step of fixing the position of the x-ray sensor relative to the region of interest includes placing the x-ray sensor in the mouth of a subject and the subject holding the bite bar between their teeth.

17. The method of claim 15, wherein the positional information provided by the inertial sensor is used to determine the relative position of the x-ray source and the digital x-ray detector for each image.

18. The method of claim 15, wherein the processor calculates a motion correction factor based on the relative position of the x-ray source and the digital x-ray detector for each image.

19. The method of claim 15, wherein the detection of said x-rays occurs without any mechanical connection between the x-ray sensor and x-ray source.

20. The method of claim 15, wherein operating the x-ray sensor to detect said x-rays comprises capturing images for each emitter position in a sequence; and the method comprises
    correcting the image for each emitter position in the sequence for apparent emitter position; and
    generating final x-ray images.

* * * * *